(12) United States Patent
Abe

(10) Patent No.: US 9,308,129 B2
(45) Date of Patent: Apr. 12, 2016

(54) OPHTHALMIC LASER TREATMENT APPARATUS

(71) Applicant: NIDEK CO., LTD., Gamagori-shi, Aichi (JP)

(72) Inventor: Hitoshi Abe, Okazaki (JP)

(73) Assignee: NIDEK CO., LTD., Gamagori (JP)

( * ) Notice: Subject to any disclaimer, the term of this patent is extended or adjusted under 35 U.S.C. 154(b) by 0 days.

(21) Appl. No.: 14/703,275

(22) Filed: May 4, 2015

(65) Prior Publication Data

US 2015/0230986 A1    Aug. 20, 2015

Related U.S. Application Data

(62) Division of application No. 13/073,217, filed on Mar. 28, 2011, now Pat. No. 9,050,170.

(30) Foreign Application Priority Data

Mar. 31, 2010   (JP) ................................. 2010-084684

(51) Int. Cl.
*A61B 18/18*     (2006.01)
*A61F 9/008*     (2006.01)
(Continued)

(52) U.S. Cl.
CPC ... *A61F 9/00821* (2013.01); *A61B 2018/00589* (2013.01); *A61B 2018/00988* (2013.01); *A61B 2018/2085* (2013.01); *A61F 2009/00863* (2013.01); *A61F 2009/00897* (2013.01)

(58) Field of Classification Search
CPC ............. A61F 2009/00878; A61B 2018/2085; A61B 2009/00897
USPC ........................................................ 606/4–6
See application file for complete search history.

(56) References Cited

U.S. PATENT DOCUMENTS 5,906,609 A    5/1999 Assa et al.
5,938,657 A    8/1999 Assa et al.
(Continued)

FOREIGN PATENT DOCUMENTS

CN    101553280 A    10/2009
EP    1 210 915 A2    6/2002
(Continued)

OTHER PUBLICATIONS

Feb. 12, 2015 Office Action issued in U.S. Appl. No. 13/073,256.
(Continued)

*Primary Examiner* — William Thomson
*Assistant Examiner* — John R Downey
(74) *Attorney, Agent, or Firm* — Oliff PLC

(57) ABSTRACT

An ophthalmic laser treatment apparatus for treating an eye including: an irradiation unit including a laser source, and a scanner for scanning an irradiation spot from the laser source onto a tissue of the eye in two dimensions; a memory for storing a plurality of predetermined irradiation patterns in each of which a plurality of the irradiation spots are arranged in a predetermined arrangement; an irradiation pattern selecting unit including a switch for inputting a signal to select a pattern from the patterns stored in the memory; an pattern changing unit including a switch for inputting a signal to change part of the arrangement of the irradiation pattern in which irradiation spots are arranged on the basis of the selected irradiation pattern; and a control unit for controlling driving of the irradiation unit to sequentially irradiate the beam based on the irradiation pattern changed by the pattern changing unit.

4 Claims, 7 Drawing Sheets

(51) Int. Cl.
    *A61B 18/00*    (2006.01)
    *A61B 18/20*    (2006.01)

(56) References Cited

U.S. PATENT DOCUMENTS

| | | | |
|---|---|---|---|
| 6,099,522 A * | 8/2000 | Knopp et al. | 606/10 |
| 6,585,725 B1 | 7/2003 | Mukai | |
| 6,673,061 B2 | 1/2004 | Abe | |
| 7,173,745 B2 | 2/2007 | Dair et al. | |
| 2002/0099363 A1 | 7/2002 | Woodward et al. | |
| 2004/0073200 A1 | 4/2004 | Caudle et al. | |
| 2006/0100677 A1* | 5/2006 | Blumenkranz et al. | 607/89 |
| 2007/0121069 A1 | 5/2007 | Andersen et al. | |
| 2007/0129775 A1 | 6/2007 | Mordaunt et al. | |
| 2007/0189664 A1 | 8/2007 | Andersen et al. | |
| 2008/0015553 A1 | 1/2008 | Zacharias | |
| 2009/0093798 A1 | 4/2009 | Charles | |
| 2011/0178512 A1 | 7/2011 | Blumenkranz et al. | |
| 2011/0202046 A1 | 8/2011 | Angeley et al. | |

FOREIGN PATENT DOCUMENTS

| | | |
|---|---|---|
| JP | H02-161930 A | 6/1990 |
| JP | 2001-149403 A | 6/2001 |
| JP | 2002-224154 A | 8/2002 |
| JP | 2002-524144 A | 8/2002 |
| JP | 2006-524515 A | 11/2006 |
| JP | 2009-514564 A | 4/2009 |
| WO | 00/13629 A1 | 3/2000 |
| WO | 2005/065116 A2 | 7/2005 |
| WO | 2007/035855 A2 | 3/2007 |
| WO | 2007/082102 A2 | 7/2007 |
| WO | 2008/112292 A1 | 9/2008 |

OTHER PUBLICATIONS

U.S. Appl. No. 13/073,256, filed Mar. 28, 2011 in the name of Abe.
U.S. Appl. No. 13/073,278, filed Mar. 28, 2011 in the name of Yokosuka et al.
European Search Report issued in European Patent Application No. 11160163.9 mailed Aug. 8, 2011.
European Search Report issued in European Patent Application No. 11160416.1 mailed Jul. 13, 2011.
Dec. 13, 2012 Office Action issued in U.S. Appl. No. 13/073,278.
Jan. 2, 2013 Office Action issued in U.S. Appl. No. 13/073,256.
Aug. 13, 2013 Office Action issued in U.S. Appl. No. 13/073,256.
Aug. 19, 2013 Office Action issued in U.S. Appl. No. 13/073,278.
Jun. 5, 2014 Office Action issued in U.S. Appl. No. 13/073,256.
Feb. 4, 2014 Office Action issued in Japanese Patent Application No. 2010-084684.
Sep. 1, 2015 Office Action issued in Japanese Patent Application No. 2014-078436.

* cited by examiner

OPHTHALMIC LASER TREATMENT APPARATUS

CROSS-REFERENCE TO RELATED APPLICATIONS

This is a Division of application Ser. No. 13/073,217 filed Mar. 28, 2011, which claims the benefit of Japanese Patent Application No. 2010-084684, filed Mar. 31, 2010. The disclosure of the prior applications is hereby incorporated by reference herein in its entirety

TECHNICAL FIELD

The present invention relates to an ophthalmic laser treatment apparatus for treatment a patient's eye by irradiation a laser beam thereto.

BACKGROUND ART

As one of ophthalmic laser treatment apparatuses, a photocoagulation apparatus is known. For photocoagulation treatment (e.g., panretinal photocoagulation treatment), a treatment laser beam is sequentially irradiated on a spot-by-spot basis to fundus tissues of a patient's eye to thermally photocoagulate the tissues. For irradiation of the treatment laser beam, a visible aiming beam is first irradiated for aiming of the treatment laser beam (for example, see JP 2002-224154A). In recent years, an apparatus has been proposed in which a scanning unit including a galvano mirror and others is installed in a laser-beam delivery unit to scan a treatment laser beam in the form of a spot onto fundus tissues based on a plurality of irradiation patterns of spot positions set in advance (for example, see JP 2006-524515A and JP 2009-514564A). This apparatus stores in advance a plurality of predetermined irradiation patterns in a memory, for example, a pattern of spots arranged in a square matrix of 3×3, 5×5, or others, a pattern of spots arranged in a circular form (including a fan-like form), and others so that a desired irradiation pattern is selectable by an operator according to the condition of the tissues. Further, the aiming beam is also irradiated based on the irradiation patterns.

SUMMARY OF INVENTION

Technical Problem

Meanwhile, the irradiation patterns stored in the memory are typical arrangement patterns of spots. All combination patterns are not always prepared in advance. If all irradiation patterns are stored in the memory, a selection procedure to select a desired pattern is complex and hence operationality is poor. However, if only the previously prepared irradiation patterns are available, one or some spots may fall on a treatment area to which laser irradiation should be avoided according on the condition of the area.

For instance, the case where an irradiation pattern of 5×5 spots is selected for irradiating a laser beam to a wide range of eye fundus is assumed. After termination of laser irradiation to a region T1, when a laser beam is to be irradiated to an adjacent region T2 according to the 5×5 irradiation pattern as shown in FIG. 4A, a part of the spots, i.e., spots S14 and S25, are likely to fall on a blood vessel V. For avoiding laser irradiation to the blood vessel V, when a 4×4 pattern is selected and a laser beam is irradiated to a region T2a, a remaining part of the region T2 has to undergo laser irradiation of another pattern or each one spot as shown in FIG. 4B. These works are troublesome for an operator and lower treatment efficiency. Even if an apparatus includes a function of freely designing spot positions according to a treatment area, it takes time and labor to design all spots from first to last.

When photocoagulation is to be conducted on a circular area with a predetermined diameter (e.g., an annular area centered on the macula) on the fundus, a circular arc pattern (a circular arc irradiation pattern of spots arranged in a circular arc with a predetermined curvature) is selected from the irradiation patterns stored in the memory. The laser beam of this circular arc pattern is repeated plural times to arrange the spots in a circular form. However, even when only the laser irradiation in the selected circular arc pattern is repeated plural times, the spots could not be arranged in the circular form depending on the condition and the curvature of the fundus of the patient's eye. For instance, if photocoagulation is conducted on a wide area of the fundus based on a skewed irradiation pattern because the curvature of the circular arc pattern does not conform with the curvature of the fundus, the spots are not irradiated at uniform intervals onto the fundus. If various circular arc patterns having different curvatures are stored in the memory, a selection procedure to select a circular arc pattern with a desired curvature is complex, leading to poor operationality. Even if the apparatus has the function of freely designing the spot positions, such operation needs much time and labor to design all the spots into a circular pattern with a desired curvature.

The present invention has been made to solve the above problems and has a purpose to provide an ophthalmic laser treatment apparatus capable of performing efficient and appropriate treatment by effectively utilizing previously prepared irradiation patterns.

Solution to Problem

To achieve the above purpose, one aspect of the invention provides an ophthalmic laser treatment apparatus for treating a patient's eye by irradiating a treatment laser beam thereto, comprising: an irradiation unit including a treatment laser source, and a scanner for scanning an irradiation spot of the treatment beam from the laser source onto a tissue of the patient's eye in two dimensions; a memory for storing a plurality of predetermined irradiation patterns in each of which a plurality of the irradiation spots of the treatment beam are arranged in a predetermined arrangement; an irradiation pattern selecting unit including a selection switch for inputting a signal to select a desired irradiation pattern from the irradiation patterns stored in the memory; an irradiation pattern changing unit including a change switch for inputting a signal to change a part of the arrangement of the irradiation pattern in which the irradiation spots are arranged on the basis of the selected irradiation pattern by the irradiation pattern selecting unit; and a control unit for controlling driving of the irradiation unit to sequentially irradiate the treatment beam based on the irradiation pattern changed by the irradiation pattern changing unit.

Advantageous Effects of Invention

According to the present invention, it is possible to perform efficient and appropriate treatment by effectively utilize previously prepared irradiation patterns.

DESCRIPTION OF EMBODIMENTS

Figure 1:
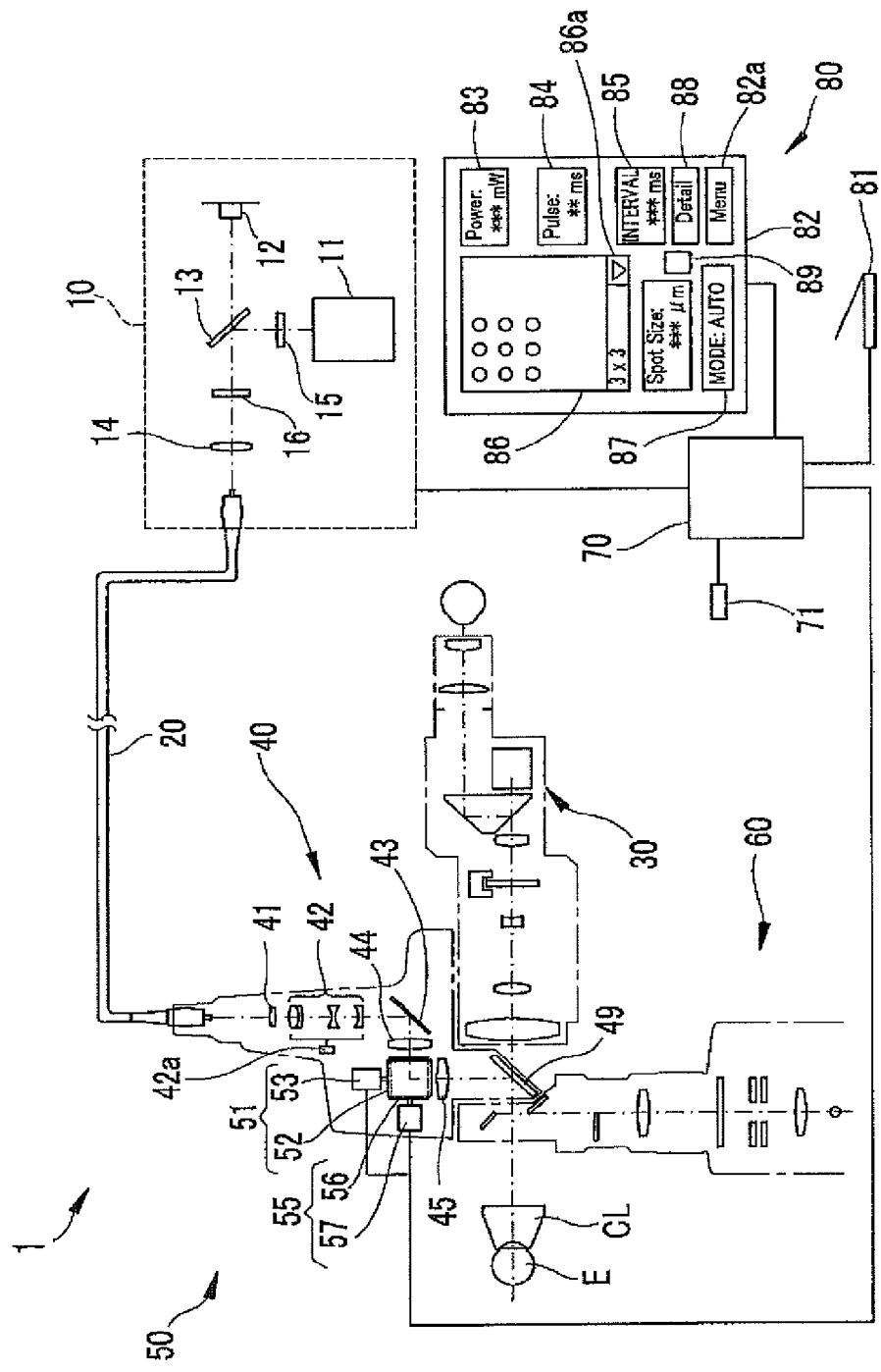
FIG. 1 is a schematic configuration view of optical systems and a control system in an ophthalmic laser treatment apparatus.

A detailed description of a preferred embodiment of the present invention will now be given referring to the accompanying drawings. FIG. 1 is a schematic configuration view showing optical systems and a control system in an ophthalmic laser treatment apparatus for performing photocoagulation treatment of a fundus, and others.

An ophthalmic laser treatment apparatus 1 roughly includes a laser source unit 10, a laser irradiation optical system 40, an observation optical system 30, an illumination optical system 60, a controller 70, and an operation unit 80. The laser source unit 10 includes a treatment laser source 11 for emitting a treatment laser beam, an aiming light source 12 for emitting a visible aiming laser beam (an aiming beam), a beam splitter (a combiner) 13 for combining the treatment laser beam and the aiming beam, and a focusing lens 14. The beam splitter 13 reflects most of the treatment laser beam and transmits a part of the aiming beam. The combined laser beam is focused by the focusing lens 14 to enter an incident end face of an optical fiber 20 for delivering the laser beam to the laser irradiation optical system 40. A first shutter 15 is placed between the laser source 11 and the beam splitter 13 to block the treatment laser beam. Further, a second shutter 16 is placed on an optical path of the aiming beam from the aiming light source 12 and the treatment laser beam from the treatment laser source 11. The second shutter 16 is a safety shutter that is closed in case an abnormality occurs, but also may be used for enabling or blocking irradiation of the aiming beam during scanning of the aiming beam. The first shutter 15 also may be used for enabling or blocking irradiation of the treatment laser beam. Each shutter may be replaced with a galvano mirror having a function of switching optical paths.

The laser irradiation optical system 40 is configured as a delivery unit (an irradiation unit) mounted in a slit lamp (not shown) in the present embodiment. A laser beam (the treatment laser beam and the aiming beam) emitted from the optical fiber 20 passes through a relay lens 41, zoom lenses 42 movable in an optical axis direction to change a spot size of the laser beam, a mirror 43, and a collimator lens 44. The laser beam then passes through a scanner 50, an objective lens 45, and a reflection mirror 49 and is irradiated onto a fundus of a patient's eye E. The scanner 50 consists of a scanning optical system including a scanner mirror for moving an irradiation direction (an irradiation position) of the laser beam in two dimensions. The scanner 50 includes a first galvano mirror (a galvano scanner) 51 and a second galvano mirror 55. The first galvano mirror 51 includes a first mirror 52 for reflecting the laser beam and an actuator 53 serving as a drive part for driving (rotating) the mirror 52. Similarly, the second galvano mirror 55 includes a second mirror 56 and an actuator 57. The laser beam having passed through each optical element of the laser irradiation optical system 40 is reflected by the reflection mirror 49 and irradiated onto the fundus which is a target plane (onto the tissues) of the eye E through a contact lens CL.

The zoom lenses 42 are held in a lens cam not shown. The lens cam is rotated by operation of an operator to move each zoom lens 42 in an optical axis direction. The positions of the zoom lenses 42 are detected by an encoder 42a attached to the lens cam. The controller 70 receives positional information (a detection signal) of each lens from the encoder 42a and obtains a spot size of the laser beam. The scanner 50 is controlled based on a command signal from the controller 70 to form the laser beam (the spot) in a two-dimensional pattern on the target plane. The reflection mirror 49 is connected to a mechanism (a hand-operated manipulator), not shown, which is operated by the operator, to tilt the optical axis of the laser beam in two dimensions.

Figure 2:
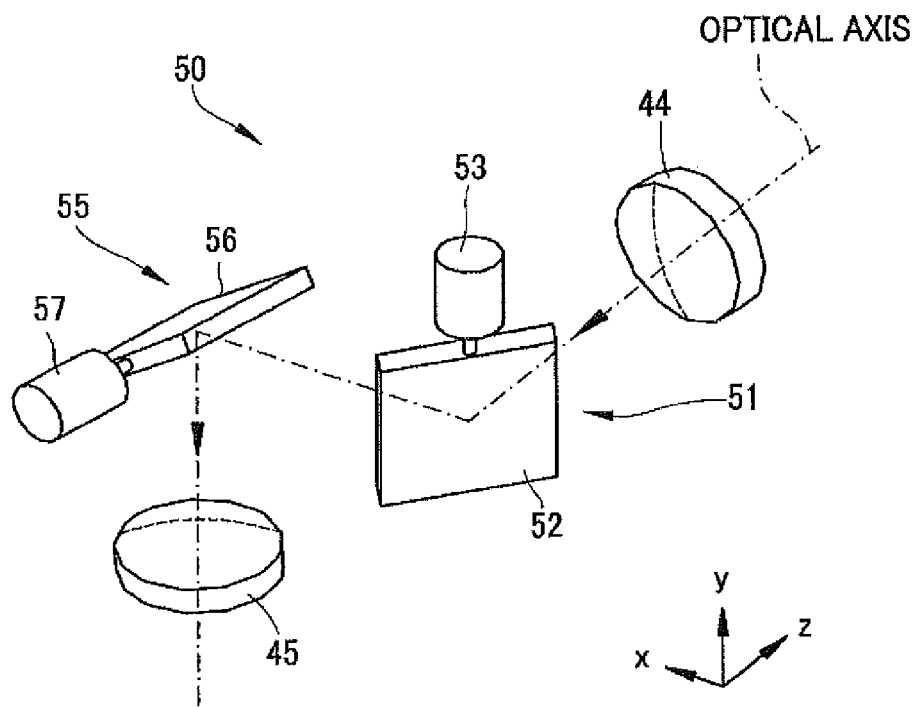
FIG. 2 is a perspective view of a scanner.

The structure of the scanner 50 will be explained. FIG. 2 is a perspective view of the scanner 50. The mirror 52 is attached to the actuator 53 to swing a reflection plane in an x-direction. On the other hand, the mirror 56 is attached to the actuator 57 to swing a reflection plane in a y-direction. In the present embodiment, the rotation axis of the mirror 52 coincides with a y-axis and the rotation axis of the mirror 56 coincides with a z-axis. Further, the actuators 53 and 57 are connected to and separately driven by the controller 70. Each of the actuators 53 and 57 contains a motor and a potentiometer (both not shown). The mirrors 52 and 56 are independently rotated (swung) based on command signals from the controller 70. At that time, positional information representing how much the mirrors 52 and 56 have been rotated is transmitted from the potentiometers of the actuators 53 and 57 to the controller 70. Accordingly, the controller 70 ascertains the rotational positions of the mirrors 52 and 56 with respect to the command signals.

The observation optical system (an observation unit) 30 and the illumination optical system (an illumination unit) 60 are installed in the slit lamp. The observation optical system 30 includes an objective lens and further a variable magnification optical system (a variable magnification unit), a protection filter, erect prisms, a field diaphragm, eyepieces, and others. The illumination optical system 60 for illuminating the eye E with slit light includes an illumination light source, a condenser lens, a slit, a projection lens, and others.

To the controller 70, there are connected a memory 71, the light sources 11 and 12, the encoder 42a, the actuators 53 and 57, the operation unit 80, and a footswitch 81 serving as a device for inputting a trigger for irradiation of the laser beam. The operation unit 80 includes a touch panel display 82 used for setting laser irradiation conditions, and changing and inputting irradiation patterns. The display 82 is provided with various panel switches (for inputting a designation signal and others) for setting parameters of the laser irradiation conditions. Further, signals are input in regard to the coordinates of the display 82, thus enabling input of a signal to designate a spot position and others. The display 82 has a graphical user interface function enabling a user to visually check and set numerical values and others. For items of the irradiation conditions, there are prepared a setting part 83 for output power of the treatment laser beam, a setting part 84 for an irradiation time (a pulse width), a setting part 85 for a halt time (a time interval of irradiation of the treatment laser beam), a setting part 86 for irradiation patterns of the treatment laser beam (arrangement patterns of spot positions of the treatment laser beam to be formed on the target plane), a mode setting part 87 (a mode selector) for setting an aiming mode, a details setting switch 88, a Menu switch 82a for calling up other setting parts and others, etc. With the mode setting part 87, a plurality of aiming modes is selectively set.

At the touch of each item on the display 82, numeral values can be set. For instance, when an operator touches the switch 86a, selectable options are displayed in a pull-down menu. When the operator chooses a numeral value from the options, a set value in that item is determined. A plurality of irradiation patterns (or scanning patterns) is previously prepared to be selectable by the operator on the display 82. As the irradiation patterns prepared by an apparatus manufacturer, for example, there are a pattern of spots arranged in a square matrix of 2×2, 3×3, 4×4 or other (a square pattern), a pattern of spots arranged in a circular arc form (a circular arc pattern), a pattern of spots arranged in an outer circumferential direction and an inner circumferential direction to form a fan-like form (a fan-like pattern), a pattern of spots arranged in a circular form (a circular pattern), a divisional pattern of the circular pattern (a circular divisional pattern), a linear pattern of spots arranged in a linear form, and other patterns. They are stored in the memory 71. The irradiation pattern is selectable from the plurality of irradiation patterns stored in the memory 71 by use of the switch 86a on the setting part 86. A selected irradiation pattern is displayed on the screen of the setting part 86. Further, the information of the spot size of the laser beam changed by movement of the zoom lenses 42 is displayed on the display 82.

When the footswitch 81 is pressed down by the operator, the controller 70 irradiates the laser beam based on the settings of various parameters to form a pattern of the treatment laser beam on the target plane. Specifically, the controller 70 controls the light source 11 and controls the scanner 50 based on the set pattern to form the pattern of the treatment laser beam on the target plane (the fundus).

Figure 3:
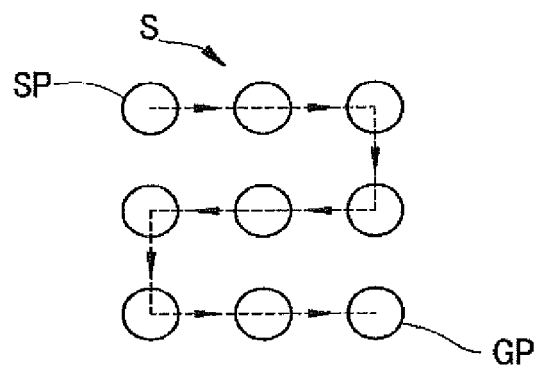
FIG. 3 is a view showing one example of patterns.

FIG. 3 shows one example of the patterns of spot positions. As shown in the figure, this pattern is configured by arranging spots S in a 3×3 square matrix. Herein, the spots S represent both the aiming beam and the treatment laser beam. Based on such pattern, the treatment laser beam and the aiming beam are scanned by the scanner 50 to form the pattern on the target plane. The spot S starts to be irradiated from a start position SP and is scanned toward an end position GP in two dimensions. In the present embodiment, as indicated by arrows in the figure, the laser beam is scanned to sequentially move from one to adjacent spots S so as to enable movement between spots S as efficient as possible.

The interval between the spots S can be arbitrarily set in a range from 0.5 to 2 times the spot diameter by use of the spot interval setting part 89 on the display 82. In the case of the square pattern shown in FIG. 3, the spots S are arranged at equal intervals in vertical and horizontal directions.

In the apparatus configured as above, treatment operations by irradiating the treatment laser beam will be explained below. This apparatus is provided with a pattern changing function of changing a part of arrangement of the irradiation pattern in which the spots are arranged on the basis of an irradiation pattern selected by the switch 86a or changing the shape of spot arrangement. As an example of the pattern changing function of the present apparatus, a pattern changing function of changing a part of the arrangement of the irradiation pattern in which the spots are arranged on the basis of the irradiation pattern is first explained, in which one or some spots are deleted from or added to the spots in the selected irradiation pattern. Prior to a surgical operation, conditions for the operation are set. For panretinal photocoagulation treatment, it is assumed that a spot size of the treatment laser beam is set to 200 μm and a 5×5 square pattern is selected as the irradiation pattern in advance, respectively.

The operator observes the fundus illuminated by illumination light from the illumination optical system 60, through the observation optical system 30, and also observes the spot position of the irradiated aiming beam, and moves the slit lamp (including the observation optical system 30 and the illumination optical system 60) containing the laser irradiation optical system 40 with respect to the eye E to aim the beam to a treatment area. During aiming, the aiming light source 12 and the scanner 50 are controlled to operate based on the selected irradiation pattern so that the operator observes the spot position in the irradiation pattern by visual persistence of the aiming beam. Specifically, at each spot position, the driving of the galvano mirrors 51 and 55 of the scanner 50 is stopped and the aiming beam is irradiated with a pulse width of constant time. During movement of the spot to a next position, the aiming beam is not irradiated. If the speed (cycle) of one scan to each spot position is higher than the visual persistence time of a human eye, all the spots are simultaneously observed by the operator. If the speed of one scan is slower than the visual persistence time, all the spots are not simultaneously observed. Thus, the operator can identify the irradiation order of the spots.

After the aiming beam is aligned with the treatment area by the operator who observes the aiming beam, irradiation of the treatment laser beam is started upon input of a trigger signal from the footswitch 81. At each spot position, the driving of the galvano mirrors 51 and 55 is stopped and the treatment laser source 11 is driven to irradiate the treatment laser beam for a set irradiation time. During movement of the spot, the emission of the laser beam from the treatment laser source 11 is stopped. The driving of the scanner 50 and the driving of the treatment laser source 11 are controlled based on the irradiation pattern, thereby sequentially irradiating the treatment laser beam to each spot position.

The operator moves the slit lamp installed with the laser irradiation optical system 40 or moves the reflection mirror 49 to sequentially move the irradiation region of the 5×5 spot pattern with respect to the treatment area on the fundus and performs laser irradiation. In the course of this treatment, such a relatively wide irradiation region for the 5×5 spot pattern may fall on a portion (a thick blood vessel or others) that should not undergo laser irradiation. This case is exemplified in FIG. 4A. Specifically, after the termination of laser irradiation to the region T1, when the aiming beam is aimed at the adjacent region T2, a part of the spots, i.e., spots S14 and S25, fall on the blood vessel V. To avoid this, it is conceivable to select a 4×4 irradiation pattern or others from the irradiation patterns stored in the memory 71 and perform laser irradiation to the region T2a. However, it takes time and labor to conduct laser irradiation to the remaining part of the region T2, leading to poor efficiency.

In this case, therefore, the pattern changing function of deleting or adding one or some spots from/to the spots in the selected pattern is used. When a spot deletion/addition mode is selected by the "Menu" switch 82a on the display 82, the screen of the display 82 is changed to a screen 90 shown in FIG. 5. In an indication part 91, spots P in a currently selected irradiation pattern are graphically displayed. When a spot position(s) is touched on the screen of the indication part 91, the position(s) in which the spot(s) is to be deleted or added is designated. In the present apparatus, specifically, a touch panel function of the display 82 is used as a spot position designating device (a change signal input device). Instead of the touch panel function, the position designating device also may be configured as a switch. In this case, a cursor appearing on the screen is moved to a desired position and this position is designated by the switch.

Figure 4A:
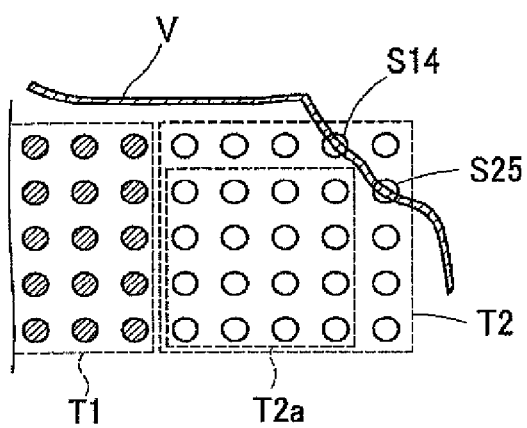
FIGS. 4A and 4B are explanatory views of laser irradiation in a 5×5 irradiation pattern.
Figure 5:
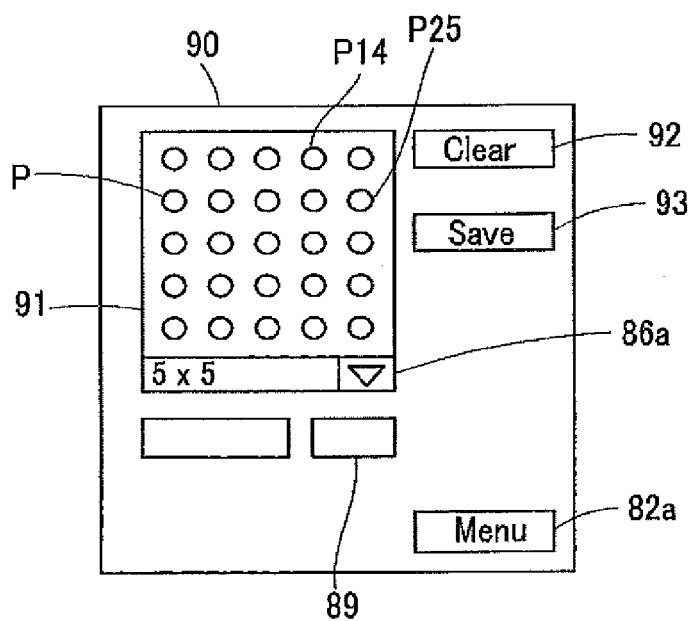
FIG. 5 is a view showing an example of a screen for an irradiation pattern changing mode related to a 5×5 irradiation pattern.

In the example shown in FIG. 5, when spot positions P14 and P25 corresponding to the spots S14 and S25 in FIG. 4A are designated, these spots are caused to disappear. Thus, the irradiation pattern is changed, so that the aiming beam and the treatment laser beam are not irradiated to the positions from which the spots deleted. The changed irradiation pattern is stored in a temporary storage area of the memory 71. When the spot positions P14 and P25 from which the spots have disappeared are designated again, these spots are displayed again on the screen.

Figure 4B:
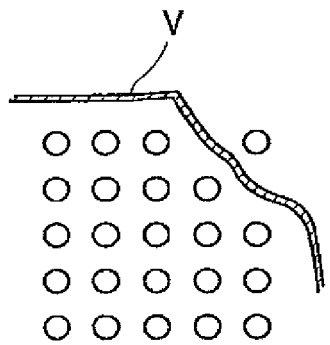

The scanner 50 and the aiming light source 12 are driven based on the changed irradiation pattern, thereby irradiating the spot of the aiming beam in the changed pattern as shown in FIG. 4B. When a trigger signal is inputted by the foot switch 81, the treatment laser source 11 is caused to emit the treatment laser beam and simultaneously the scanner 50 is activated based on the changed irradiation pattern, thereby sequentially irradiating the treatment laser beam onto the fundus. Specifically, the driving of the treatment laser source 11 and the scanner 50 is controlled to perform laser irradiation by skipping the spots S14 and S25 in FIG. 4A.

In FIG. 5, when a signal is inputted by a "Clear" switch 92, the irradiation pattern changed on the indication part 91 is cleared and returned to the original 5×5 irradiation pattern. Accordingly, for a next region, laser irradiation can be performed easily in the originally selected pattern. As an alternative, it may be arranged to clear the irradiation pattern temporarily stored in the memory 71 after the laser irradiation is executed by input of the trigger signal, and display the initial 5×5 irradiation pattern again.

Figure 6A:
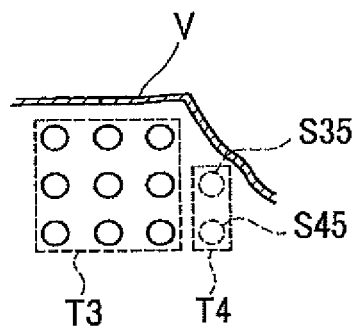
FIGS. 6A and 6B are explanatory views of laser irradiation in a 3×3 irradiation pattern.

On the other hand, an example of adding spot(s) to the selected irradiation pattern is explained below. For instance, it is assumed that a 3×3 spot pattern is selected from the irradiation patterns stored in the memory 71. When the 3×3 spot pattern is aligned with a region T3 close to the blood vessel V as shown in FIG. 6A, next 3×3 spots for a region T4 adjacent to the region T3 are likely to fall on the blood vessel V due to its state. In this case, it takes time and labor to individually irradiate the laser beam on each of spot positions S35 and S45 in the region T4. Therefore, the pattern changing function of adding spot(s) is used.

Figure 7:
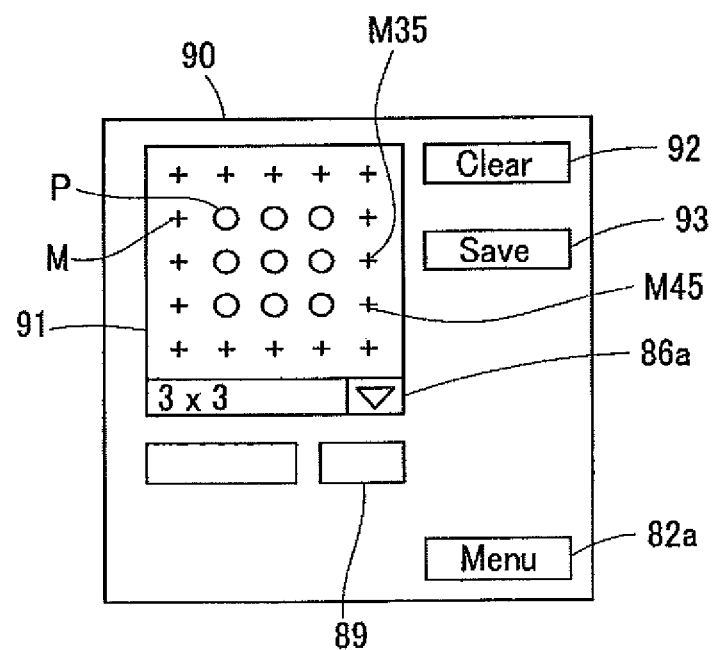
FIG. 7 is a view showing an example of a screen for an irradiation pattern changing mode related to a 3×3 irradiation pattern.

FIG. 7 is a view showing an example of a changed screen for the irradiation pattern changing mode in the case of the 3×3 spot irradiation pattern. In the indication part 91, circular spots P representing the currently selected 3×3 irradiation pattern is graphically displayed. Around the 3×3 spots P, cross marks M are displayed to represent spot positions in which spots can be added. Each cross mark M is displayed in a position determined according to an arrangement rule of spots in the selected irradiation pattern (i.e., in a position based on the arrangement rule). In this example, spots can be added up to the 5×5 square arrangement. The maximum number of addable spots is determined based on a relationship between the setting information of the spot size determined by movement of the zoom lenses 42, the setting information of spot intervals determined by the spot interval setting part 89, and a maximum scannable range.

On the screen of the indication part 91 in FIG. 7, when spot positions M35 and M45 are designated at the touch thereof, marks M located in those positions are changed to the circular marks representing the spots P. Thus, the irradiation pattern of the spot positions is changed (a change signal in inputted). The changed irradiation pattern is stored in the temporary storage area of the memory 71. The added spots P are determined according to the arrangement rule of the initially selected irradiation pattern of 3×3. In this example, specifically, the positions of additional spots are determined in a grid arrangement extending from the 3×3 pattern. It is to be noted that the additional spot position(s) is determined by snapping a position designated at the touch of the screen to a position near the touched position and defined by the arrangement rule. When the signal is inputted by the "Clear" switch 92, the irradiation pattern changed on the indication part 91 is cleared and the initially selected pattern is displayed again.

Figure 6B:
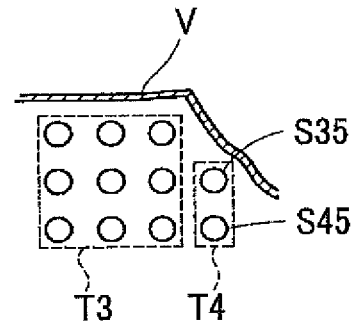

The scanner 50 and the aiming light source 12 are activated based on the changed irradiation pattern. Accordingly, the spots are additionally observed in the spot positions S35 and S45 as well as the 3×3 spots in the region T3 as shown in FIG. 6B. When the trigger signal is inputted, the treatment laser source 11 is caused to emit the treatment laser beam and the scanner 50 is activated based on the changed irradiation pattern, thereby sequentially irradiating the treatment laser beam to the spot positions in FIG. 6B. It is therefore possible to efficiently perform treatment according to the treatment area.

As above, since the irradiation pattern is changed by deleting or adding one or some spots from/to the previously prepared irradiation pattern, the treatment can be efficiently performed and the time needed for the surgical operation can be shortened. Since the previously prepared patterns are utilized, the irradiation patterns can be set more efficiently as compared with the case of designing all spot positions from first to last. Both deletion and addition of spot(s) can be applied to the selected pattern.

The irradiation pattern changed as above can be additionally stored at the press of the switch 93 into the memory 71 as one of the irradiation patterns selectable by the switch 86a. When the changed irradiation pattern is to be utilized again, the time and trouble of creating the irradiation pattern by deleting and/or adding the spot(s) as mentioned above.

As an example of the pattern changing function of changing the shape of spot arrangement with respect to the irradiation pattern selected by the switch 86a, a pattern changing function of changing a curve (a curvature) of the selected circular arc pattern will be explained below. Prior to a surgical operation, conditions for the operation are set. For panretinal photocoagulation treatment, it is assumed that a spot size of the treatment laser beam is set to 200 μm and also a circular arc pattern consisting of spots arranged in a circular arc form is selected as the irradiation pattern in advance, respectively.

Figure 8:
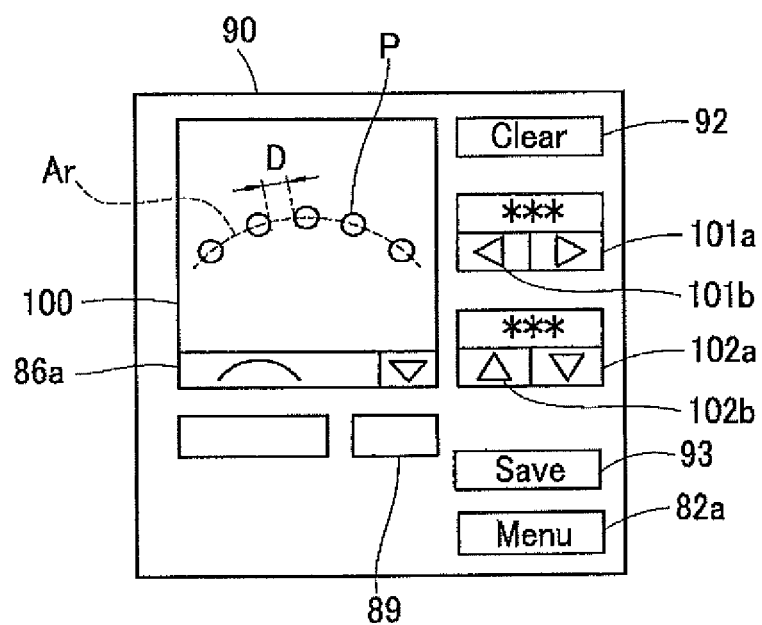
FIG. 8 is a view showing an example of a screen for a changing mode of a circular arc pattern.

FIG. 8 shows an example of a screen appearing on the display 82 when the circular arc pattern is selected by the switch 86a and the circular pattern changing mode is selected by the "Menu" switch 82a. In an indication part 100, spots P in the currently selected circular arc pattern are graphically displayed. When this circular arc pattern is to be rotated by a desired rotation angle, a signal representing the rotation angle is inputted by switches 101a and 101b. The circular arc pattern is rotated clockwise by the switch 101a and counterclockwise by the switch 101b. The signal input to rotate the circular arc pattern may be conducted by use of a touch function. For instance, when the operator touches and drags one spot P in the irradiation pattern displayed on the indication part 100 in a desired direction to rotate the irradiation pattern, the spots P are rotated relative to the center of the circular arc and a signal representing the rotation angle is inputted (the rotation angle is determined).

Figure 9A:
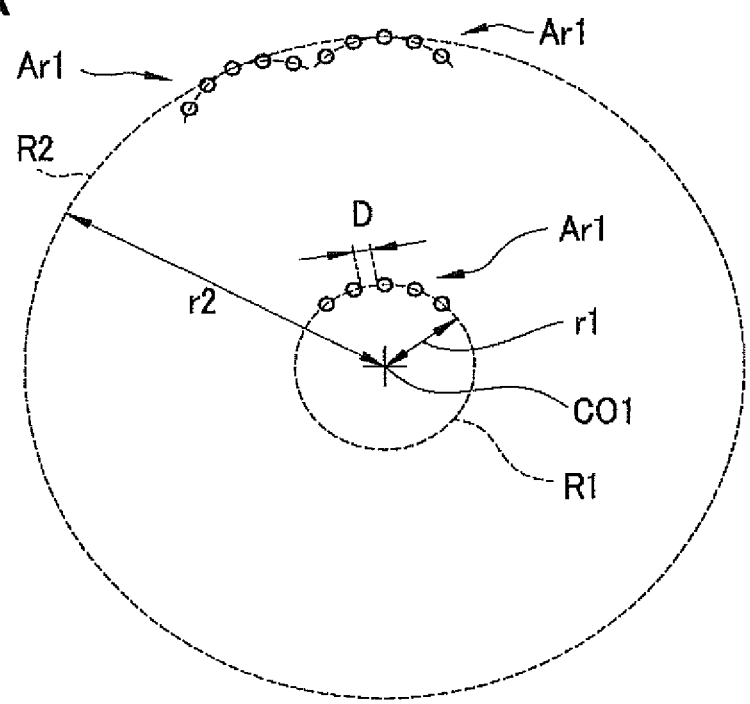
FIGS. 9A and 9B are schematic explanatory views showing a state where spots in the circular arc pattern are irradiated onto a fundus.

FIG. 9A is a schematic explanatory view showing a state where spots (an aiming beam) of a circular arc pattern are irradiated to a fundus F. For photocoagulation treatment, the spots are irradiated in a circle centered on a center CO1 (e.g., a central fovea) of the fundus F. In FIG. 9A, a circular arc pattern Ar1 is selected by the switch 86a and the curve of this pattern Ar1 is along a circle R1 with a radius r1 from the center C01. When the circular arc pattern Ar1 is to be rotated, a signal representing a rotation angle is inputted by the switches 101a and 101b, thereby rotating this pattern Ar1 along the circle R1. In FIG. 9A, the curve of the pattern Ar1 is along the circle R1 with the radius r1 from the center CO1. Accordingly, rotation of the pattern Ar1 enables the laser beam to be irradiated as spots arranged in the circle R1 with the radius r1.

However, when treatment is to be performed by arranging the spots in a circle R2 with a larger radius r2 than the radius r1, this treatment could not be conducted by use of the selected circular arc pattern Ar1. In this case, even when the pattern Ar1 is rotated, each spot is not arranged just on the circle R2. Thus, even if the laser beam is irradiated in the circular arc pattern Ar1 as it is, the treatment that arranges spots at equal intervals could not be performed. For photocoagulation on a wide area such as panretinal photocoagulation treatment (PRT) and others, preferably, a treatment laser beam is irradiated so as to arrange spots (coagulation spots) at equal intervals.

In the above case, the pattern changing function of changing the curve of a circular arc of a selected circular arc pattern is used. In FIG. 8, when switches 102a and 102b are operated, the curve of the circular arc Ar on which the spots P are arranged is changed on the indication part 100. In other words, a signal to change a curve of a circular arc pattern, which is a signal to change the irradiation pattern, is inputted by the operation of the switches 102a and 102b. The switch 102a is used to change the curve of the circular arc Ar to have a smaller diameter and the switch 102b is used to change the curve of the circular arc Ar to have a larger diameter. At that time, even when the curve of the circular arc Ar is changed, the spot interval D is set by the controller 70 so as to approximately coincide with a previously set value. This enables laser irradiation of the spots arranged at equal intervals.

Figure 9B:
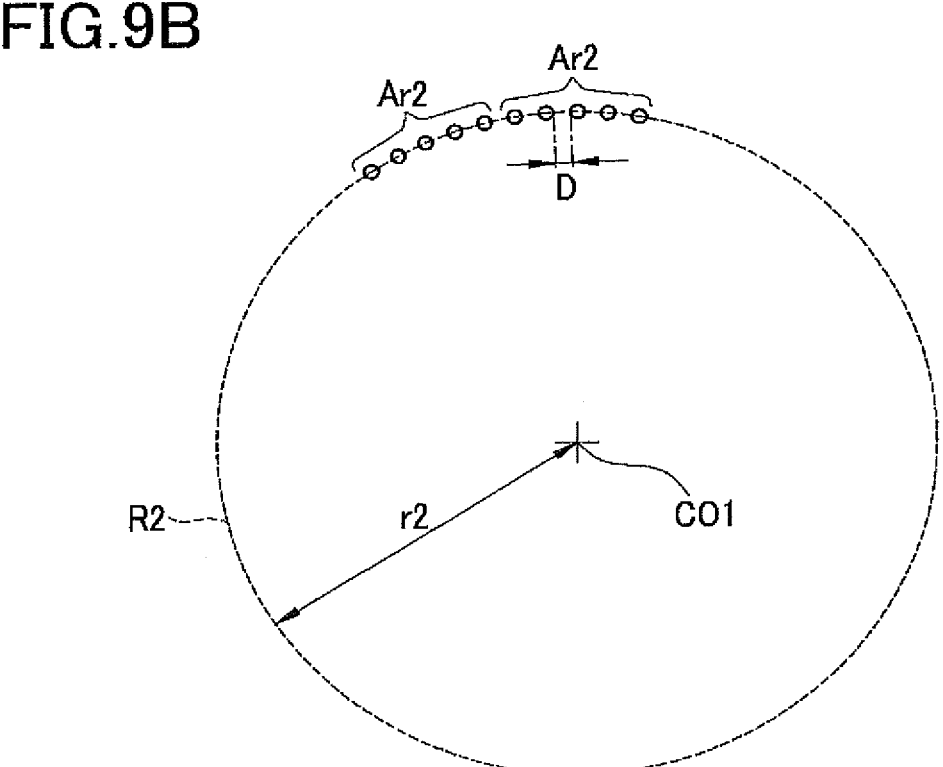

The operator operates the switches 102a and 102b for change of curve, adjusts the curve of the circular arc pattern while observing the aiming beam scanned based on the irradiation pattern (a pattern on the fundus), and changes to a circular arc pattern Ar2 so as to coincide with the circle R2 of a treatment area according to the curve (the curvature) of the fundus as shown in FIG. 9B. Accordingly, it is easy for the operator to set the irradiation pattern while observing the aiming beam in real time. Since the rotation angle of the circular arc pattern Ar2 is set by the switches 101a and 101b, the spots in the pattern Ar2 can be arranged along the circle R2 of the treatment area. Positioning of the pattern Ars in rightward/leftward and upward/downward directions can be performed by moving the slit lamp including the optical systems or two-dimensionally tilting the reflection mirror 49 by a manipulator.

Figure 10A:
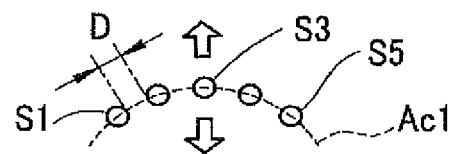
FIGS. 10A, 10B, and 10C are views showing an example of changing a curve (a curvature) of a circular arc pattern.
Figure 10B:
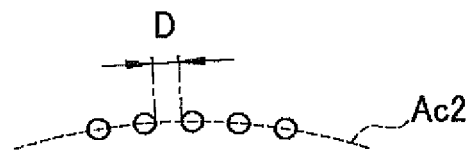
Figure 10C:
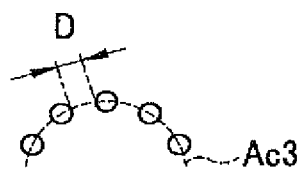

Changing the curve of the circular arc pattern may be performed on the indication part 100 by the touch panel function of the display 82, instead of using the switches 102a and 102b. For instance, as shown in FIG. 10A, a center spot S3 is touched and dragged upwards or downwards with respect to the displayed spots in the initially selected circular arc pattern, thereby changing a curve (a curvature) Ac1 of the circular arc pattern. As the curve changes, the arrangement form of the spots is changed. When the spot S3 is dragged downwards, as shown in FIG. 10B, the curve Ac1 is changed to a gentler curve Ac2. When the spot S3 is dragged upwards, as shown in FIG. 10C, the curve Ac1 is changed to a sharper curve Ac3. It is to be noted that the curve of the circular arc pattern may be changed to an elliptic form by dragging. Touching and dragging a leftmost spot S1 or a rightmost spot S5 in FIG. 10A can also freely change the curve. As above, the use of the touch function of the display 82 allows free change of the curve (the curvature) of the circular arc pattern. In the case where the curve of the circular arc pattern is changed as above, the arrangement of the spots S is set by the controller 70 so that the spot intervals D between the spots S are maintained as (almost equal to) a value set by the spot interval setting part 89. This enables irradiation of the laser beam with the uniform spot arrangement.

It is convenient to use the curve changing function for the circular arc pattern in combination with the aforementioned pattern changing function of deleting or adding the spot(s). For instance, when the circular arc pattern Ar2 is rotated to arrange new spots in a position continuous or adjacent to the previous spots along the circle R2 or an initially or previously irradiated area as shown in FIG. 9B, if one or some of the new spots are likely to overlap the previous spot(s), the pattern is changed by deleting the spot(s) which are likely to overlap the previous spot(s). On the other hand, if one or some spots are short when the circular arc pattern Ar2 is rotated to be continuous with another pattern Ar2, the pattern is changed by adding one or some spots.

Further, in the similar manner to the above case for deletion/addition of spot(s), the changed circular arc pattern can be additionally stored at the press of the switch 93 into the memory 71 as one of the irradiation patterns selectable by the switch 86a. When the changed pattern is to be utilized again, it is therefore possible to save the time and trouble of creating the changed irradiation pattern.

As above, treatment can be performed by setting the circular arc pattern can according to the curved target plane (herein, the fundus F). Accordingly, the spots of the treatment laser beam can be equally spaced over the wide range of the fundus. This makes it possible to effectively conduct treatment such as photocoagulation. Since the apparatus is configured to change the curve of the previously prepared circular arc pattern, there is no need to design the circular arc pattern for each patient's eye, resulting in improved efficiency in surgical operations. In the above embodiment, the circular arc pattern is explained as the pattern consisting of the spots arranged in a line. This includes patterns (a fan-like pattern, a circular segmental pattern) consisting of spots arranged in plural circular-arc lines. The above function of changing the circular patterns may be effectively applied to these patterns.

The present invention may be embodied in other specific forms without departing from the essential characteristics thereof. For instance, the scanner 50 may include a member for e.g. tilting a single mirror in x- and y-directions. As an alternative, scanning of a laser beam or the like may be conducted by tilting a lens.

REFERENCE SIGNS LIST

1 Ophthalmic laser treatment apparatus
10 Laser source unit
20 Optical fiber
30 Observation optical system
40 Laser irradiation optical system
50 Scanner
60 Illumination optical system
70 Controller
80 Operation unit
90 Screen
100 Indication part

The invention claimed is:

1. An ophthalmic laser treatment apparatus for treating a patient's eye by irradiating a treatment laser beam thereto, comprising:
   a treatment laser source;
   an optical scanner configured to scan an irradiation spot of the treatment laser beam from the treatment laser source onto a tissue of the patient's eye in two dimensions;
   a memory configured to store a plurality of irradiation patterns in each of which a plurality of the irradiation spots are arranged in a predetermined arrangement, the irradiation patterns including a circular arc pattern in which the plurality of the irradiation spots are arranged in a circular arc form;
   a user interface configured to:
      input a selecting signal to select a desired irradiation pattern from the irradiation patterns stored in the memory; and
      input a curvature changing signal to change a curvature of the circular arc pattern; and
   a processor configured to, in response the curvature changing signal,
      change the curvature of the selected circular arc pattern based on the curvature changing signal while automatically maintaining intervals between the spots that are adjacent in the selected circular arc pattern; and
      control driving of the treatment laser source and the optical scanner to sequentially irradiate the treatment laser beam based on the circular arc pattern whose curvature is changed.

2. The ophthalmic laser treatment apparatus according to claim 1, wherein
   the user interface is configured to input a rotation signal to rotate the circular arc pattern, and
   the processor is configured to:
      rotate the selected circular arc pattern based on the input rotation signal; and
      control driving of the treatment laser source and the optical scanner based on the rotated circular arc pattern.

3. The ophthalmic laser treatment apparatus according to claim 1, wherein
   the user interface includes a touch panel for displaying the selected irradiation pattern, and
   the processor is configured to rotate the circular arc pattern with reference to a center of a curve of the circular arc pattern in a direction to which a touched point on the touch panel is dragged.

4. The ophthalmic laser treatment apparatus according to claim 1, wherein the circular arc pattern includes a pattern consisting of a plurality of spots arranged in plural circular-arc lines.

* * * * *